United States Patent
Phillips

(10) Patent No.: US 7,281,410 B2
(45) Date of Patent: Oct. 16, 2007

(54) METHOD FOR DETERMINING AN EFFECTIVE PECLET NUMBER FOR A MEMBRANE ADSORBER DEVICE

(75) Inventor: Michael W. Phillips, Tyngsborough, MA (US)

(73) Assignee: Millipore Corporation, Billerica, MA (US)

( * ) Notice: Subject to any disclaimer, the term of this patent is extended or adjusted under 35 U.S.C. 154(b) by 0 days.

(21) Appl. No.: 11/503,791

(22) Filed: Aug. 14, 2006

(65) Prior Publication Data

US 2006/0273008 A1    Dec. 7, 2006

Related U.S. Application Data

(62) Division of application No. 10/285,240, filed on Oct. 31, 2002.

(51) Int. Cl.
  *G01N 15/08*    (2006.01)
  *B01D 61/00*    (2006.01)
(52) U.S. Cl. .......................... 73/38; 201/644; 201/650; 201/651; 201/739
(58) Field of Classification Search ............... 210/644, 210/650, 651, 739; 73/38, 40
See application file for complete search history.

(56) References Cited

U.S. PATENT DOCUMENTS

| | | | |
|---|---|---|---|
| 2,788,901 A | 4/1957 | Boeddinghause et al. |
| 3,158,532 A | 11/1964 | Pall et al. |
| 4,007,113 A | 2/1977 | Ostreicher |
| 4,007,114 A | 2/1977 | Ostreicher |
| 4,305,782 A | 12/1981 | Ostreicher et al. |
| 4,340,482 A | 7/1982 | Sternberg |
| 4,347,208 A | 8/1982 | Southall |
| 4,618,533 A | 10/1986 | Steuck |
| 4,895,806 A | 1/1990 | Le et al. |
| 4,923,901 A | 5/1990 | Koester et al. |
| 4,944,879 A | 7/1990 | Steuck |

(Continued)

FOREIGN PATENT DOCUMENTS

GB    563687    8/1944

(Continued)

OTHER PUBLICATIONS

The International Search Report dated May 23, 2003 (PCT/US02/32504).

(Continued)

*Primary Examiner*—John Kim
(74) *Attorney, Agent, or Firm*—Nields & Lemack

(57) ABSTRACT

The method for determining an effective Peclet number for a membrane adsorber device includes the steps of (a) equilibrating the membrane adsorber device with an equilibration buffer at a known pH and conductivity; (b) challenging the membrane with a known concentration of a specific solute in said equilibration buffer; (c) monitoring the breakthrough of the solute downstream of the membrane as a function of a value selected from the group consisting of time, challenge volume and other suitable variable related to total quantity of material challenged to membrane adsorber device; (d) analyzing the solute breakthrough curve to determine pertinent flow characteristics of said membrane adsorber device by calculating the sharpness of the breakthrough curve of the membrane adsorber device and (e) comparing the results calculated in step (d) to results from known integral devices to determine the effective Peclet number.

13 Claims, 10 Drawing Sheets

U.S. PATENT DOCUMENTS

| | | | |
|---|---|---|---|
| 5,019,270 A * | 5/1991 | Afeyan et al. | 210/656 |
| 5,085,749 A * | 2/1992 | Grimshaw et al. | 204/541 |
| 5,085,784 A | 2/1992 | Ostreicher | |
| 5,128,037 A | 7/1992 | Pearl et al. | |
| 5,137,633 A | 8/1992 | Wang | |
| 5,147,542 A | 9/1992 | Proulx | |
| 5,176,828 A | 1/1993 | Proulx | |
| 5,282,964 A * | 2/1994 | Young et al. | 210/321.8 |
| 5,348,982 A | 9/1994 | Herbolzheimer et al. | |
| 5,433,847 A * | 7/1995 | Rice | 210/198.2 |
| 5,531,899 A | 7/1996 | Yen et al. | |
| 5,547,760 A | 8/1996 | Tarbet et al. | |
| 5,618,433 A | 4/1997 | Tarbet et al. | |
| 5,629,084 A | 5/1997 | Moya | |
| 5,679,249 A | 10/1997 | Fendya et al. | |
| 5,760,183 A | 6/1998 | Dazey et al. | |
| 5,814,372 A | 9/1998 | Moya | |
| 5,824,217 A | 10/1998 | Pearl et al. | |
| 5,922,200 A | 7/1999 | Pearl et al. | |
| 5,928,588 A | 7/1999 | Chen et al. | |
| 5,951,972 A | 9/1999 | Daley et al. | |
| 5,980,987 A | 11/1999 | Tarbet et al. | |
| 6,365,395 B1 | 4/2002 | Antoniou | |

FOREIGN PATENT DOCUMENTS

| | | |
|---|---|---|
| GB | 599909 | 3/1948 |
| WO | 00/09239 | 2/2000 |
| WO | 01/83077 | 11/2001 |

OTHER PUBLICATIONS

The International Search Report dated Jun. 2, 2003 (PCT/US02/34960).

Tejeda A et al.: "Optimal design of affinity membrane chromatographic columns" Journal of Chromatography A, Elsevier Science, NL., vol. 830, No. 2, Jan. 15, 1999, pp. 293-300, p. 294, p. 299.

Roper D K et al.: "Separation of biomolecules using adsorptive membranes" Journal of Chromatography A, Elsevier Science, NL., vol. 702, No. 1/2, May 19, 1995, pp. 3-26, abstract.

Lapidus, et al., "Mathematics of Adsorption I Beds. IV. The Effect of Longitudinal Diffusion in Ion Exchange and Chromatographic columns", J. Phys. Chem. 56, 984 (1952).

ACS Publications; Xianfang Zeng; October 29, 1999; "Membrane Chromatography: Preparation and Applications to Protein Separation" Abstract.

* cited by examiner

METHOD FOR DETERMINING AN EFFECTIVE PECLET NUMBER FOR A MEMBRANE ADSORBER DEVICE

This application is a divisional of U.S. Ser. No. 10/285,240 filed on Oct. 31, 2002, the disclosure of which is incorporated herein by reference.

The present invention relates to an adsorber membrane and a device containing it for removing selected components from a liquid stream. More particularly, it relates to a membrane based adsorber device having a membrane and a device containing one or more such membranes, each with a Peclet number (Pe) of greater than 100.

BACKGROUND OF THE INVENTION

The use of membrane chromatography or normal flow membrane based adsorbers is well known; see U.S. Pat. No. 4,895,806 and *Membrane Chromatography: Preparation and Applications to Protein Separation*, Zeng, X, Biotechnol. Prog 1999, vol 15, p. 1003-1019.

All of these devices are basically formed of a housing having an inlet and an outlet and one or more layers of an adsorptive membrane located between the inlet and outlet such that all liquid entering the inlet must flow through the one or more membrane layers before reaching the outlet. The membranes are typically rendered adsorptive by surface modification, in situ copolymerization or grafting, direct formation from adsorptive materials or by the inclusion of adsorptive particles (such as chromatography media) in the membrane matrix during formation of the membrane. In this way, one or more constituents of the liquid stream are bound to the membrane surface and removed from the stream. After completion of the filtration step, the bound material is then eluted by adding a different solution or changing pH conditions or by other well known methods in the art and either disposed of or processed and used for whatever purpose.

Typically, the material removed is the protein of interest. The remainder of the materials in the stream, such as viruses, endotoxins, nucleic acids, host cell proteins and the like pass through the device unhindered and are removed from the system.

Some have suggested removing the trace contaminants such as viruses, endotoxins, nucleic acids, host cell proteins and the like from the stream instead of removing the protein of interest. Traditionally, this has been done through the use of chromatography columns containing media with quaternary amine chemistry. This approach has several advantages such as higher yields of the product of interest. However, it has several disadvantages. For one, the use of columns results in a significant underutilization of the capacity of the column components, typically less than 1%. Moreover, the process is time consuming often taking hours to complete due in large part to long residence time required for the stream to be in the presence of the chromatography media. Lastly, the cost of the media, additional buffers, along with the QC and validation costs associated with their use, significantly impact the economics of using chromatography columns for this application.

The potential of using membrane-based adsorbers in lieu of chromatography media has been mentioned to overcome the above problems. However, the current devices have their own set of problems that need to be overcome. The problem with these devices has been that they are not efficient and are therefore expensive to make and operate. The mere adding of layers does not increase the efficiency. Instead it merely adds to the expense of the manufacture of the device and its operation. Some have tried various flow distribution devices such as tapered end plates and screens similar to what is traditionally used in chromatography columns to improve efficiency. Yet the overall results have not been satisfactory.

What is needed is a membrane adsorber device that is efficient, utilizes its capacity, has high throughput and preferably is disposable so as to eliminate the need for cleaning and revalidation of the device before reuse. The present invention provides such a membrane and device, especially for trace contamination removal.

SUMMARY OF THE INVENTION

The present invention is an adsorber membrane and a device containing one or more such membranes. Both the membrane and the device have a Peclet number (Pe) of at least 100. The membrane and the device are designed for the removal of trace contaminants in protein containing streams such as exist for example in the biopharmaceutical industry. A preferred membrane has tight pore size distribution, uniform capture mechanism densities and capacities (regardless of whether the capture mechanism is ligand based or otherwise) and high permeabilities that allow for high throughput separations.

A device of the present invention can contain a flat sheet membrane such as a pleated filter, a tangential flow filter or a spiral wound filter. Preferably, the device is formed in a stacked disk arrangement where one or more layers of membrane are sealed to each of the two large surface of the disk. One such device is formed of a series of disks, each disk having eight layers of membranes sealed to each of the two large surfaces of the disk. These disks are placed within a sealed capsule having an inlet on one end and an outlet on the other. The disks are sealed so that all fluid that exits the outlet does so by having first passed through the membranes on one side of a disk. Such a device is linearly scalable.

IN THE DRAWINGS

DETAILED SPECIFICATION OF THE INVENTION

The level of trace contaminants in feed stream can vary but they are typically low, generally in the parts per million (ppm) range or lower and the desire is to remove those contaminants such as viruses, endotoxins, DNA and host cell proteins to non-detectable levels. For example, in a typical feedstream, one has virus levels at from 1 to 10 ppm, DNA at 100 picograms/mL, endotoxins at 10EU (endotoxins units)/mL and host cell proteins at from about 10 to about 100 nanograms/mL. Removing these contaminants effectively and efficiently is a difficult task.

It has been discovered that an efficient membrane based adsorber device can be made for use in protein purification by utilizing a membrane and device configuration, each of which has a Peclet number (Pe) of at least 100. When the membrane and device both have a Pe of 100 or greater, one achieves high retention and efficiency with good flow and yield characteristics. Additionally, one is able to make a device that is linearly scalable which is of great benefit to the user.

The Peclet number (Pe) is derived from Peclet analysis and relates to the generation of a breakthrough curve for contaminants. Basically, a test material (that is representative of the trace contaminant) is flowed through a selected adsorptive membrane or device and the amount of the test material that is in the filtrate is measured. The valves are plotted on a graph with volume on the X-axis and breakthrough % on the Y-axis. For low Pe values, such as those below 10, the breakthrough of test material appears nearly immediately, well below the capacity of the membrane device, i.e. exhibiting poor efficiency. For higher Pe values, such as above 100 and preferably above 1000, the breakthrough curve begins to approach ideality and breakthrough corresponds to the capacity of the device, i.e. high efficiency.

Figure 1:
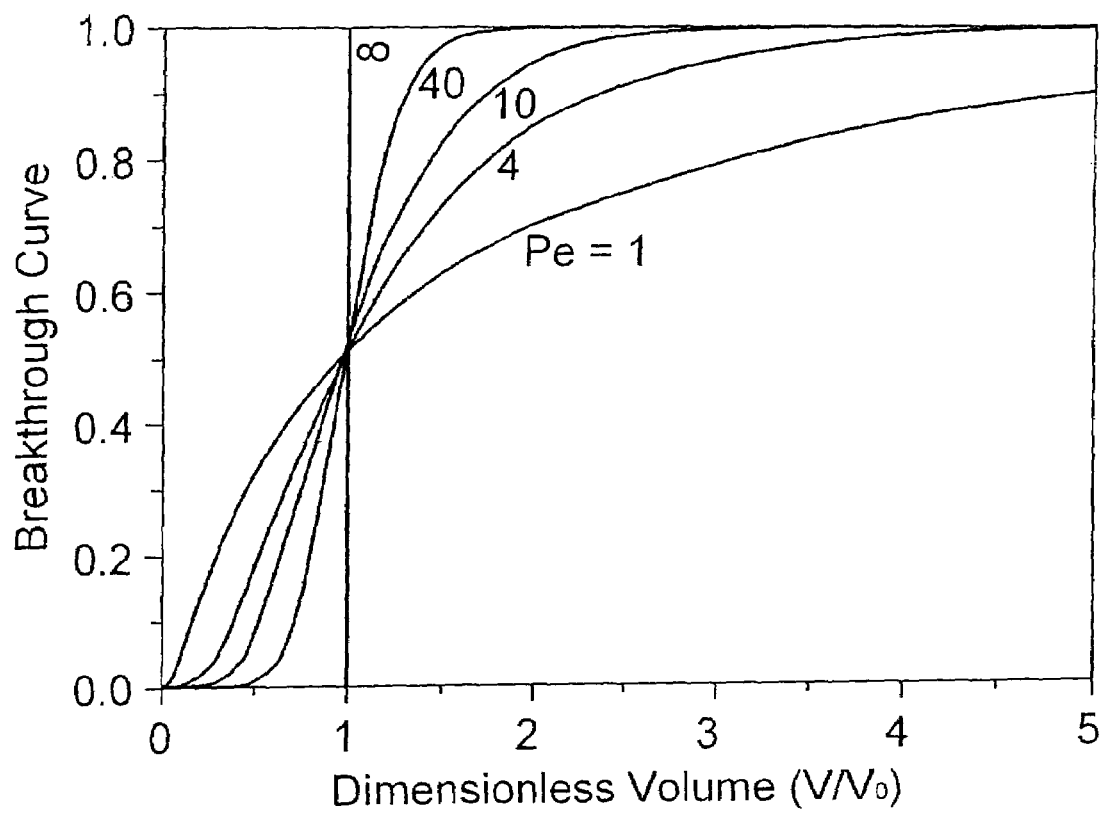
FIG. 1 shows a graph of a series of Pe values.

FIG. 1 shows the theoretical plot of Pe values described above. The ideal plot is a vertical line. The closer the curve becomes to vertical, the higher the Pe value.

For adsorptive applications, such as trace contaminant removal in validated biopharmaceutical applications, breakthrough is the critical issue, as contamination of the filtrate at any appreciable level is not allowed. It has been found that the Pe value is an important predictor of adsorptive performance of membranes and devices containing them.

Additionally, with viral removal the Pe value appears to correlate to the LRV of the membrane and device. LRV means log reduction value and is represented by the ratio of two numbers. In viral applications it is represented by the number of viral particles that are contained on the upstream side of the filter to the number of viral particles found in the filtrate. Therefore a LRV of 4 means that the membrane was challenged with $10^4$ particles and only one was found in the filtrate. The log of this ratio being 4. This means that the membrane is capable of removing 99.99% of all viral particles.

Ion exchange capacity is not an acceptable predictor of performance in adsorptive devices for trace contaminant removal as all devices have excess capacity relative to the volume of contaminant to be removed. The issue is ensuring that the contaminant, often present in the ppm range, is removed efficiently and as completely as possible.

A method used by Applicant to determine the Peclet number of a membrane (housed in a device optimally designed to minimize upstream and downstream dead volumes while affording adequate fluid distribution to effectively challenge entire membrane area) or device containing one or more membranes is as follows:

(1) Equilibrating the membrane or membrane adsorber device with an equilibration buffer at a known pH and conductivity.

(2) Challenging the membrane or membrane adsorber device with a known concentration of a specific solute in the equilibration buffer. The selection of the specific solute is typically based upon its ability (or inability) to bind to the adsorber by a specific mechanism and its ability to be readily detected downstream (various chromophores for UV detection, fluorescently labeled solutes, etc.). The selection of the challenge solute concentration is typically based upon both the thermodynamic principles associated with solute adsorption (adsorption isotherm characteristics) and the specific objectives of the test. For example, if the objective of the test were to characterize the performance of a specific membrane adsorber device, one would select buffer and solute conditions and concentrations such that the solute binding characteristics to the membrane adsorber were within the linear part of the solute adsorption isotherm. However, if the objective of the test was to characterize the flow characteristics through only the membrane (thereby minimizing the effects of upstream dead volume) one would typically select buffer and solute conditions and concentrations such that the solute binding characteristics to the membrane adsorber were within the non-linear part of the solute adsorption isotherm.

(3) Using a suitable detector, monitor the breakthrough of the solute downstream of the membrane adsorber as a function of time, challenge volume, or other suitable variable related to total quantity of material challenged to membrane adsorber.

(4) Analyze the solute breakthrough curve to determine pertinent flow characteristics of the membrane adsorber device. This analysis could include (a) calculating the sharpness of the breakthrough curve. One such means for calculating breakthrough curve sharpness is by calculating an effective Peclet number (Pe), details of which are described below. High Pe values are associated with uniform flow through the membrane adsorber, uniform density and distribution of the capture mechanism and effective distribution of flow to the entire membrane adsorber surface. A device with a high Pe number would most likely have good trace impurity retention characteristics. Low Pe values are associated with poor flow distribution properties associated with the membrane adsorber device, excessively large flow dispersive characteristics of the membrane adsorber, poor capture mechanism distribution and/or densities or a combination of two or more of these. Low Pe values may indicate that trace impurity retention characteristics are compromised.

(b) monitoring the time (or other suitable variable related to total quantity of material challenged to membrane adsorber) at either initial onset of solute breakthrough or at a specific fraction of solute breakthrough (e.g., 5% or 10%). Premature breakthrough of the solute relative to some standard (e.g., 50% breakthrough) may indicate the presence of defects that may compromise trace impurity retention characteristics. The ability to detect premature breakthrough is highly dependent upon the breakthrough curve sharpness, as calculated above in step (a). For example, the detection of defects in membrane adsorber devices that exhibit very sharp breakthrough curves is much easier than in devices in which the breakthrough curve is very diffuse. The sharpness of breakthrough curves can be enhanced by utilizing membranes with inherently high Pe numbers, designing membrane adsorber devices with low dead volumes and good flow distribution properties, by exploiting the thermodynamics of non-linear adsorption, or by a combination of any of the above.

(c) calculating both the breakthrough curve sharpness and initial onset of solute breakthrough (a combination of steps (a) and (b)). In this manner, defects and/or flow distribution properties (either membrane or device related) that may compromise trace impurity retention characteristics could be detected.

(5) Comparing the results calculated in step (4) to results from known integral devices, thereby determining either the integrity of the membrane adsorber or membrane adsorber device or the ability of such a device for removing trace impurities.

As stated above, one such means of determining the sharpness of a breakthrough curve is by calculating an effective Peclet number (Pe). Breakthrough curves are typically sigmoidal in shape (s-shaped). Lapidus and Amundson (Lapidus, L. and N. R. Amundson, "Mathematics of adsorption in beds. VI. The effect of longitudinal diffusion in ion-exchange and chromatographic columns," *J. Phys. Chem.*, 56, 984 (1952).) developed a mathematical model that related the shape of the breakthrough curve to various model parameters, given by:

$$\frac{C_A}{C_0} = \frac{1}{2}\left\{1 + \text{erf}\left[\frac{(Pe)^{1/2}(V - \bar{V})}{2(V\bar{V})^{1/2}}\right]\right\} \quad \text{equation (1)}$$

where
  $C_A$ is the effluent solute concentration
  $C_0$ is the inlet solute concentration
  V is the challenge volume
  $V_{bar}$ is the challenge volume at 50% breakthrough ($C_A/C_0$=0.5)
  Pe is the Peclet number From a technical point of view, this equation was derived for linear systems. However, this form of equation can be used to interpret any breakthrough curve. Accordingly, an effective Pe can be determined by simply fitting this equation to an experimentally determined breakthrough curve. Various means for fitting breakthrough curve data to this equation include (a) a least-squares fit by which all the data is simultaneously used to determine a best-fit (one which minimizes the least-squares error) (b) a multipoint method by which a discreet number of points (2 or 3) are used (c) or any of several other methods. An example of method (b) is to use equation (1) to make a generic plot of Pe versus $$\frac{V_{90} - V_{10}}{V_{50}},$$

where $V_{10}$, $V_{50}$, and $V_{90}$ and the breakthrough volumes corresponding to 10, 50, and 90% solute breakthrough, respectively. Then, from the experimental breakthrough curve, determine the values for $V_{10}$, $V_{50}$, and $V_{90}$. Then, from the generic Pe plot, determine the effective Pe number. It should be noted, however, that this is only one means by which the sharpness of the breakthrough curves can be quantified.

While the above process is the preferred means for obtaining a Pe of a membrane or device, others methods can be developed that would quantify the breakthrough curve sharpness and thereby provide one with the same type of relevant information. It is meant by this invention to encompass and include those methods within the teachings of the present invention.

The membrane of the present device must have a Peclet number that is sufficiently high to accomplish the level of contaminant removal that is desired. Typically, the membrane(s) itself will have a Pe of from about 100 to greater than 10,000. Preferably, it is at least 100, more preferably at least 200, even more preferably at least 500 or at least 1000 and most preferably at least 10,000 or greater.

It has been found that the device Pe will typically be equal to or lower than the Pe of the membrane. To date, no device has been found that is capable of having a Pe higher than the Pe of the membrane. A variety of device properties such as poor flow distribution, the method of membrane incorporation into the device (pleating, stacked disk, other methods) and the like can adversely affect the Pe number of the device. Therefore, the use of membranes having a Pe higher than the desired device Pe is recommended.

The membrane may be a microporous or macroporous membrane formed of a polymer selected from olefins such as polyethylene, including ultrahigh molecular weight polyethylene, polypropylene, EVA copolymers and alpha olefins, metallocene olefinic polymers, PFA, MFA, PTFE, polycarbonate, vinyl copolymers such as PVC, polyamides such as nylon, polyesters, cellulose, cellulose acetate, regenerated cellulose, cellulose composites, polysulphones, polyethersulphones, polyarylsulphones, polyphenylsulphones, polyacrylonitrile, polyvinylidene fluoride (PVDF), and blends thereof. Additionally, nonwoven and woven fabrics of the same materials, such as Tyvek® paper available from E.I. DuPont de Nemours and Company of Wilmington, Del. Likewise fibrous media such as a cellulosic pad, MIL-LISTAK+™ filtration media available from Millipore Corporation of Bedford, Mass. may be used. The membrane selected depends upon the Pe, the desired filtration characteristics, the particle type and size to be filtered and the flow desired.

The membranes selected must be capable of adsorbing one or more species from a desired stream of liquid. The membranes, such as regenerated cellulose membranes, are inherently functional such that no further treatment is required. However in most cases, the selected membrane is either not functionalized or is insufficiently functionalized such that additional treatment of the membrane is required. There are several well-known methods of rendering membrane functional. See *Membrane Chromatography: Preparation and Applications to Protein Separation*, Zeng, X, Biotechnol.Prog 1999, vol 15, p. 1003-1019. The functional characteristic may be one or more of the following: hydrophilicity, hydrophobicity, charge (positive or negative), oleophilicity, oleophobicity, and ligand chemistry.

The most common methods of rendering a membrane material functional include: incorporating a functional material into a membrane structure during formation; treating the surface of the membrane with a functionalizing material and grafting or polymerizing and crosslinking the functional material onto the surface and the use of ligands bound to the membrane surface.

One can add the material as a solid such as ion exchange resin or chromatography media into the membrane structure during formation, see U.S. Pat. No. 5,531,899. Alternatively, one can add a liquid component such as PVP into the batch material used to make the membrane to provide the desired functionality.

Preferably, one uses a surface treatment of the preformed membrane. By surface it is meant all surfaces of the membrane, the upper and lower faces as well as the inner walls of the pores in the membrane structure. This can be a monomer that is polymerized and crosslinked in place such as is taught in U.S. Pat. No. 4,944,879 or it may be a polymer such as is taught in U.S. Pat. Nos. 5,629,084 and 5,814,372. U.S. Pat. No. 5,137,633 teaches adding two components a monomer for philicity and epichlorohydrin adding a positive charge to the membrane.

Alternatively, one may graft a polymer onto the membrane surface such as is taught by U.S. Pat. No. 4,340,482 although this is not preferred due to the harsh treatment conditions imposed and the deterioration of the membrane structure that occurs under such conditions.

The above membranes as treated may be used as is or if desired, ligands such as quaternary amines can be bound to their surfaces to impart a different or increased selectivity. Typically the membrane surface is first treated to render it hydrophilic and then the ligands are attached to the membrane surface via a linker arm. See U.S. Pat. Nos. 4,923,901, 5,547,760, 5,618,433 and 5,980,987.

Any of the above methods as well as any other method that results in an adsorbing membrane can be used in the present invention.

There should be sufficient membrane in the device to provide the required Pe and capacity desired. Depending on the device configuration, this typically means more than one layer of membrane in a device. It has been found that there is a minimum number of membrane layers that are required to achieve the desired Pe in a given device format. The number required depends upon the membrane and the device format selected. Typically, it has been found that two to four layers are sufficient to give one the desired Pe. In a preferred embodiment of the present invention as shown in Example 3, one layer provided a sufficiently high Pe number, with 3 layers providing the maximum Pe obtainable with the selected membrane. Additional layers can then be added to provide the desired capacity.

Additionally, one may use two or more different membranes to achieve even greater efficiency by selecting a membrane that is most efficient for a particular contaminant. Commercial products useful in this invention include a 0.65 micron nominal pore size membrane known as Durapore® (membrane available from Millipore Corporation of Bedford, Mass. This membrane is modified to render it philic and to carry a positive charge. This membrane has a Pe of at least 2000, preferably 4000 when tested by the Peclet test described below in an eight layer format. Other membranes that are useful in the present invention include CHEMPURE 1 membranes available from Millipore Corporation of Bedford, Mass. and EMPOR membranes available from 3M of Minneapolis, Minn., both of which are membranes that incorporate particulate chromatography media into the membrane structure; regenerated cellulose membranes such as the charged PL series of membranes available from Millipore Corporation of Bedford, Mass., ICDM membrane available from Millipore Corporation of Bedford, Mass., Mustang membranes available from Pall Corporation of East Hills, N.Y. and Sartobind membranes available from Sartorius GmbH of Germany.

In designing a device that is suitable for the present invention, several factors appear to contribute to the success of the device and to the achievement of a high Pe value. First, the membrane must have a Pe of at least 100 by the Pe test defined herein. Second, the membrane selected should have a relatively inherently narrow pore size distribution. This allows one to achieve the maximum achievable Pe number for a given type of membrane. Also, this determines the minimum number of layers required to effect the separation. Further, the membrane should have as even a density of capture sites as possible throughout the membrane. It is believed that the Pe can be adversely affected by poor or non-uniform capture mechanism (e.g. poor ligand distribution) distribution in a membrane.

Additionally, one should endeavor to select a device design that will minimize the upstream dead volumes and mixing zones to maintain as even and uniform a flow as possible. Lastly, one should design the upstream and downstream fluid paths to minimize residence time distribution of various fluid paths thereby maximizing flow and keeping them as uniform as possible from point in a device to another.

An additional advantage of a properly designed device of the present invention is that the device is linearly scalable. By "linearly scalable" it is meant that one is able to design devices having a given Pe is sizes that are useful for research, pilot and production scale processes and that performance of all of the devices will be essentially the same regardless of the size of the process used. For example, this means that work done with a small scale device will allow one to select and use the same device configuration with additional area and volume and have it work with the Pe at pilot or production scale. This is a great advantage in that it eliminates the need to redesign the device at each scale and provides one with the knowledge and safety that the selected device will work for all uses when one attempts to scale up one's process to production levels. It reduces cost and time required in the scale up and it also simplifies validation of the process and device.

A device of the present invention can contain a flat sheet membrane such as a pleated filter, a tangential flow filter or a spiral wound filter. Preferably, the device is formed in a disk arrangement, more preferably a stacked disk arrangement where one or more layers of membrane are sealed to each of the two large surfaces of the disk. One such device is formed of a series of disks, each disk having two or more, preferably eight layers, of membranes sealed to each of the two-large surfaces of the disk. These disks are placed within a sealed capsule having an inlet on one end and an outlet on the other. The disks are sealed so that all fluid that exits the outlet does so by having first passed through the membranes on one side of a disk. The disk arrangement provides one with a parallel arrangement of membranes which provide for uniform and parallel fluid distribution and flow at relatively low pressure drops with little mixing or dead volume.

Figure 2:
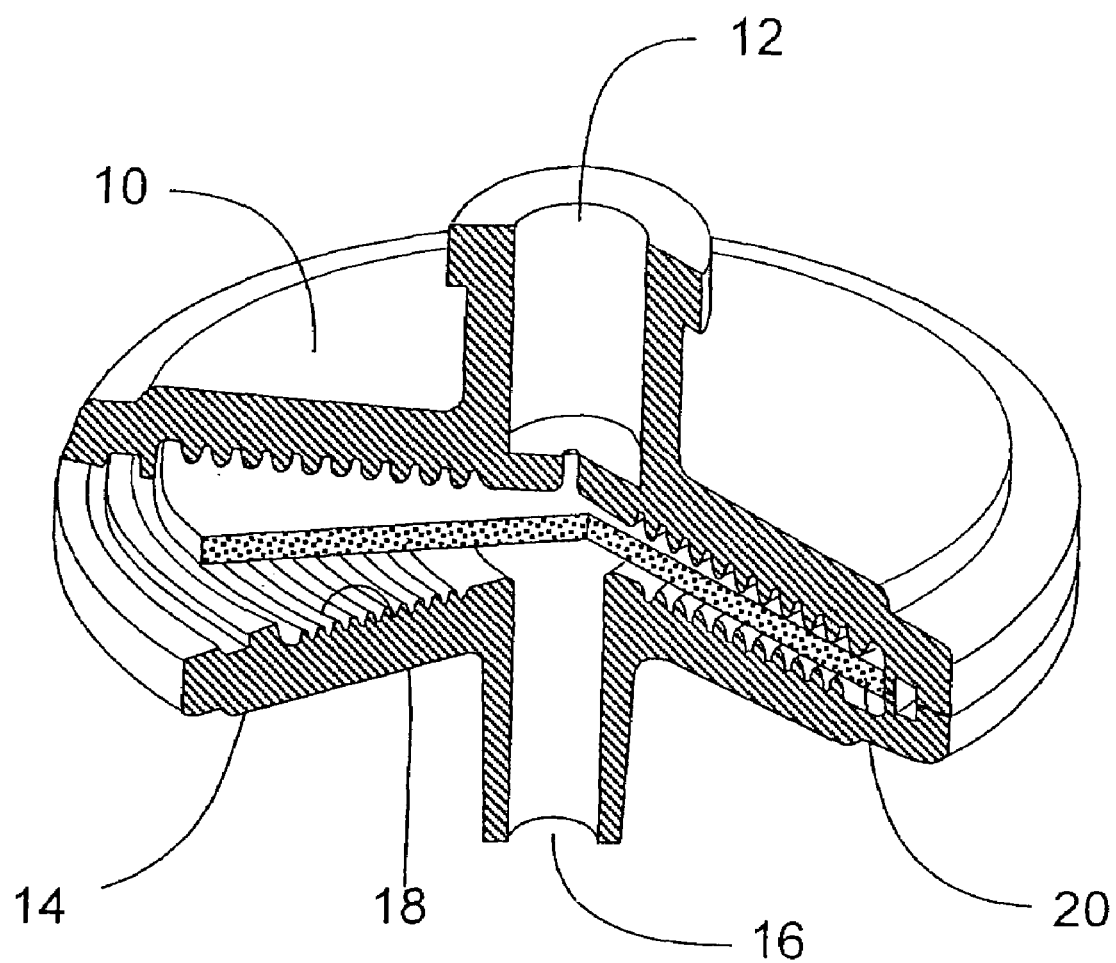
FIG. 2 shows a cutaway view of a device of the present invention according to a first embodiment of the present invention.

FIG. 2 shows a first embodiment of the device of the present invention. This device is a small scale device based on a MILLEX® device available from Millipore Corporation of Bedford, Mass. The device has a top portion 10 having an inlet 12, a bottom portion 14 having an outlet 16 and a porous membrane support platform 18. A packet of membrane 20 is sealed to the bottom portion 14 before the top portion 12 and bottom portion 14 are sealed together such that all fluid must pass through the membrane packet 20 before reaching the outlet 16. It has been found that depending upon the capacity of the membrane selected and the desired capacity of the device one can use two or more layers of membrane in the packet 20. In a preferred embodiment, a 25 mm diameter MILLEX® device was loaded with 8 layers of 0.65 hydrophilic charged DURAPORE® membrane to yield a device having 3.5 cm² frontal area and 0.35 ml bed volume.

The packet was sealed around its inner and outer edges. This was accomplished using a heat seal although other methods such as epoxy or urethane adhesives, vibrational welding or polyolefin overmolds could be used. If desired on can seal the packet in the device separately rather than as part of the device sealing process.

Figure 3:
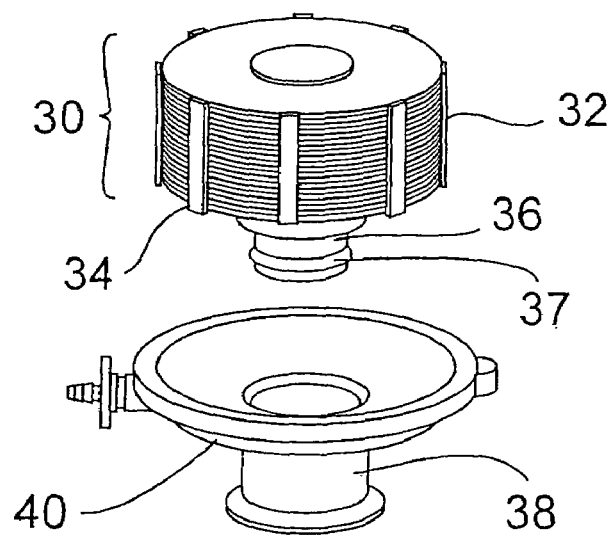
FIG. 3 shows an exploded view of a portion of a device of the present invention according to a first embodiment of the present invention.

FIG. 3 shows a portion of the stacked disk device that is useful in the present invention. This is used in large scale (pilot or production) processes. The device as shown is based on a MILLIDISK® device available from Millipore Corporation of Bedford, Mass. In this FIG. 3, a series of disks 30, each having one or more layers of adsorptive membranes bonded to each of their two major faces. The disks 30 have been spaced apart from each other and attached to each other by their outer rims to prevent distortion by spacing lugs 32. The disks are also sealed to each other by an inner sealing rim 33 shown in FIG. 5 and attached to an outlet plate 34 of the device. This outlet plate 34 is comprised of a relatively flat surface (not shown) having an outlet (not shown) in the middle of the surface and a outlet neck 36 which contains a seal 38 in this case an O-ring on its outer surface. The outlet neck 36 fits into and seals against the inner surface of the device outlet 38 of the lower housing piece 40 of device.

Figure 4:
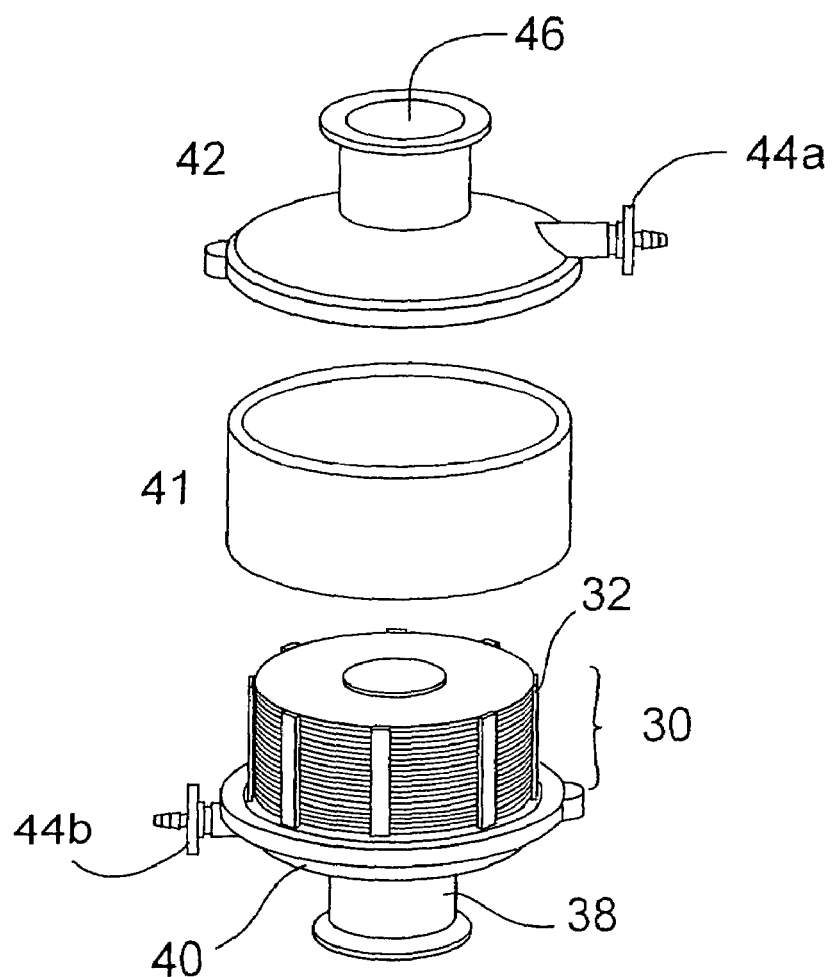
FIG. 4 shows an exploded view of a device of the present invention according to a second embodiment of the present invention.

FIG. 4 shows the entire device in an exploded view. Those parts already describe din Figure retain the same numbering as in FIG. 3. In addition to the disks 30, outlet plate 34 (shown as mounted in the device outlet 38) there is also a body 41 and an upper housing piece 42. Also shown are two vents/drains 44A and 44B. The device inlet is shown as 46. The upper housing piece 42, body 41 and lower housing piece 40 are all sealed together to form a leak proof housing. If metal, one can weld the sections together. Preferably they are all made of plastic and solvent bonded, heat bonded or plastic welded together. While the housing is shown as three pieces, it could easily be made of more or less pieces depending upon one's mold design.

Figure 5:
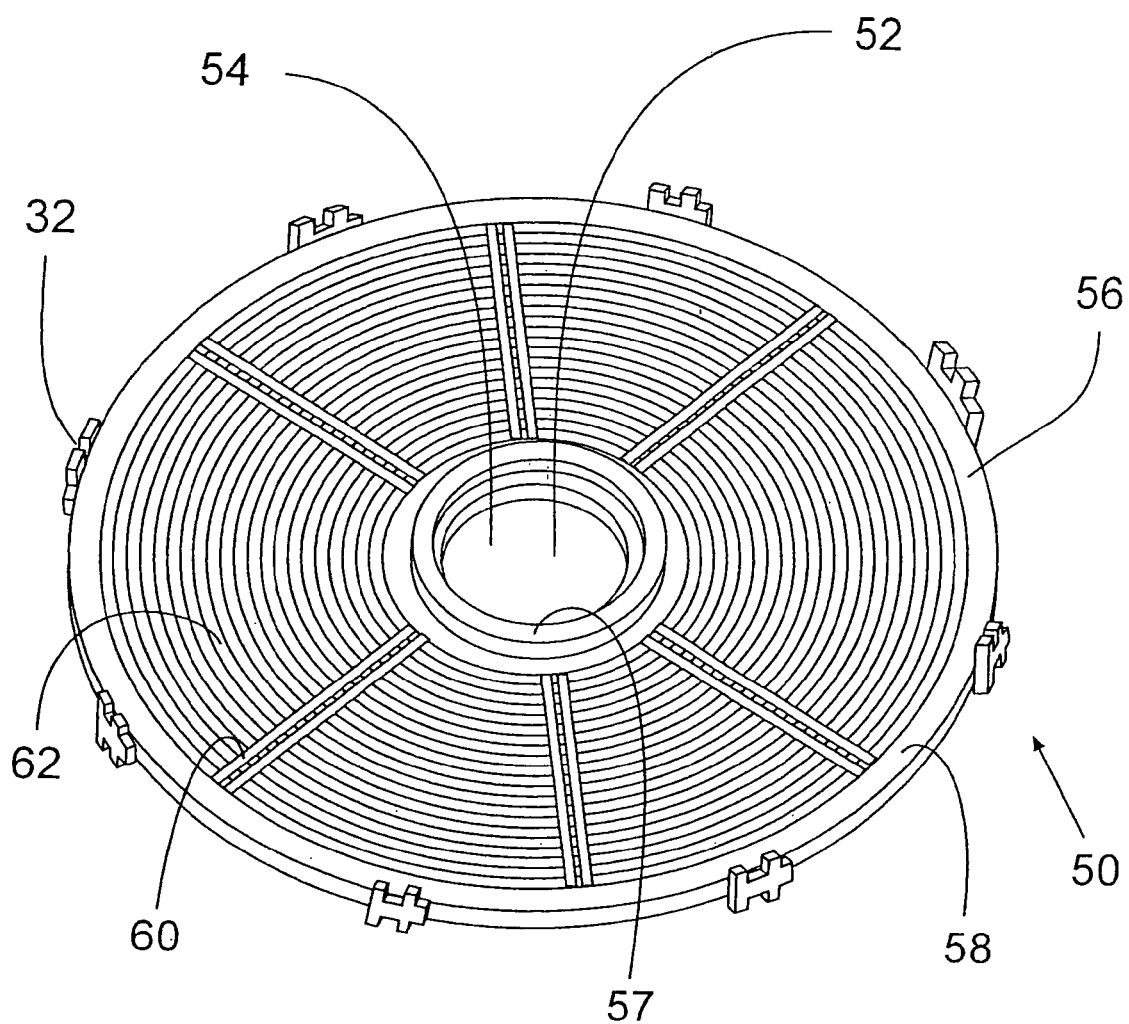
FIG. 5 shows a planar view of a disk useful in one of the embodiments of the present invention.

FIG. 5 shows a disk 50 used in the embodiment of FIG. 4. The inner rim 52 is formed adjacent a central opening 54 which serves as the outlet of the disk and a inner sealing rim 33 discussed in relation to FIG. 3. The outer rim 56 and the inner rim 52 have a flat area 57 and 58 that serve as a sealing point for the membrane(s). Also shown are a series of radial ribs 60 and concentric ribs 62 which serve to support the membrane(s) and to act as channels between the membrane(s) and the opening 54 for the fluid that has passed through the membranes. Also shown are the lugs 32 as discussed in relation to FIG. 3.

Figure 6:
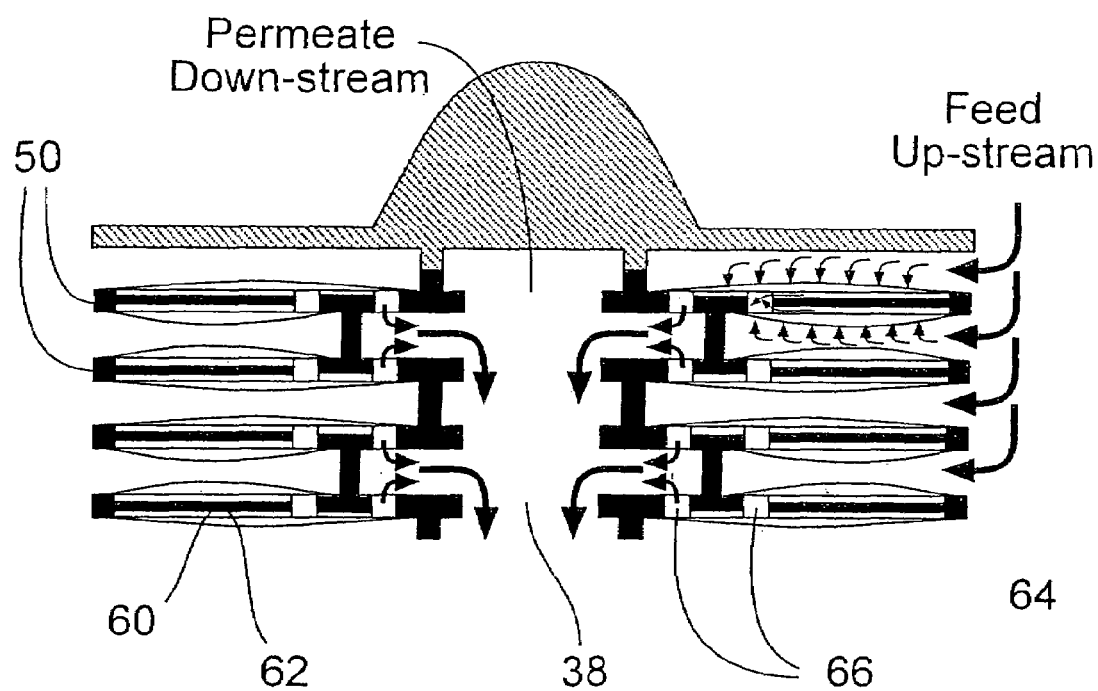
FIG. 6 shows a representative cross-section of a device according to the embodiment of FIG. 3 and the fluid flow path through it.

FIG. 6 shows a partial cross-section of a device of FIG. 4 with the fluid flow paths. Fluid is fed through the inlet (not shown) to the outside of the disks 50. Fluid enters the membrane(s) 64 sealed on each side of the disks 50. It passes along the channels formed by the ribs 60 and 62 to a flow window 66 adjacent the central opening 54 and from there it exits the device through the outlet 38.

Figure 7:
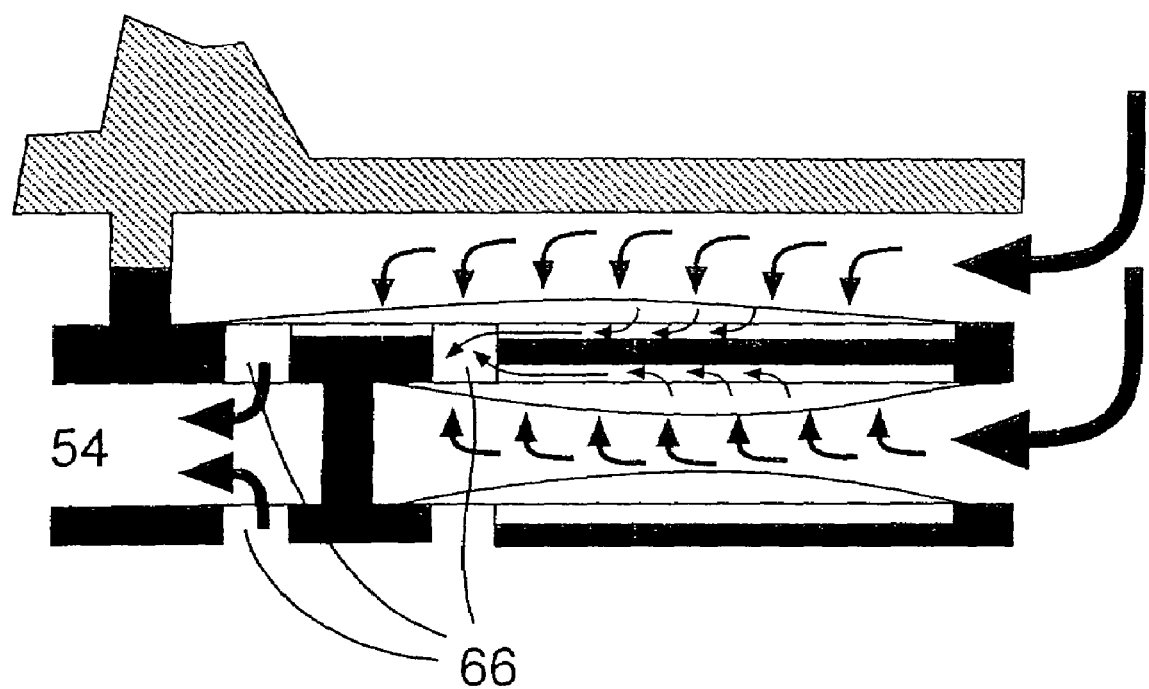
FIG. 7 shows a close view of the representative cross-section of a device according to the embodiment of FIG. 3 and the fluid flow path through it of FIG. 6.

FIG. 7 shows an even closer cross-section of the flow path through one disk of the device of FIG. 4. The flow windows 66 can be more clearly seen and they allow for the fluid to flow unhindered to the central opening 54.

In a preferred embodiment, a 3.25 inch (82.55 mm) diameter MILLIDISK® device having 6 disks, each loaded was loaded with 8 layers of 0.65 hydrophilic charged DURAPORE® membrane on each side of each disk yielded a device having 0.045 m² frontal area and 0.045L bed volume.

In another embodiment, a 3.25 inch (82.55 mm) diameter MILLIDISK® device having 60 disks, each loaded was loaded with 8 layers of 0.65 hydrophilic charged DURAPORE® membrane on each side of each disk yielded a device having 0.45 m² frontal area and 0.45L bed volume.

Other formats of devices useful in the present invention include pleated flat sheet cartridges, especially those having two or more layers of membrane, tangential flow cassettes such as are shown in U.S. Pat. Nos. 5,147,542, 5,176,828, 5,824,217 and 5,922,200 and which are commercially available as PROSTAK®, Pellicon®, Pellicon II® and Pellicon XL® cassettes from Millipore Corporation of Bedford, Mass. and spiral wound cartridges such as those taught by U.S. Pat. No. 5,128,037 and available as HELICON® cartridges from Millipore Corporation of Bedford, Mass.

The components of the device such as end caps, inlets, outlets, housings, disks, etc., can be made of a variety of materials, such as metal, ceramic, glass or plastic. Preferably, the components are formed of metal such as stainless steel, especially 316 stainless steel or aluminum due to their relatively low cost and good chemical stability or more preferably, plastics, such as polyolefins, especially polyethylene and polypropylene, homopolymers or copolymers, and ethylene vinyl acetate (EVA) copolymers; polycarbonates; styrenes; PTFE resin; thermoplastic perfluorinated polymers such PFA; PVDF; nylons and other polyamides; PET and blends of any of the above.

A method for determining the integrity of a membrane and/or a device containing one or more membranes is also part of this invention and is as follows:

The membrane or device is challenged with an adsorbing solute. The challenge buffer and solute concentration are selected such that the binding of the solute to the membrane follows Langmuir adsorption and the solute concentration is sufficient to be in the non-linear portion of the adsorption isotherm. The reason for operating in the non-linear portion of the isotherm is that favorable adsorption thermodynamics will enhance the sharpness of the solute breakthrough (to increase the test sensitivity it is important that the breakthrough be as sharp as possible). The output of the test would be the breakthrough time at a predetermined low level of breakthrough (typically less than 10%, preferably from about 1 to about 5%) and the broadness of the breakthrough front, (typically measured by the time of 5% breakthrough to 95% breakthrough relative to 50% breakthrough). This test is capable of detecting a defect in one layer of an eight layer stacked disk device as described herein. For integral membranes and device the low level break through is extremely sharp. When defects are present, premature breakthrough occurs, thereby decreasing the low level breakthrough time and in some instances adversely affecting the broadness of the breakthrough front. By plotting the data one can see if a defect is present.

Figure 8:
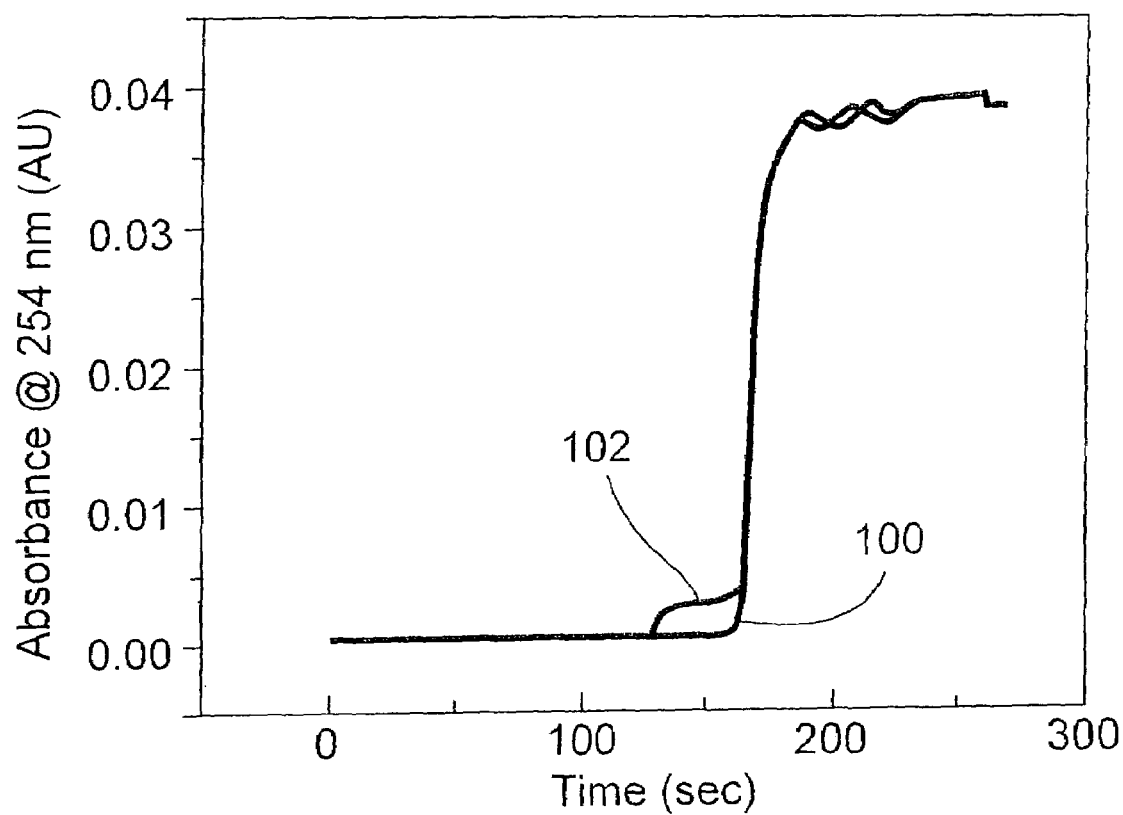
FIG. 8 shows the Pe values obtained by an integral membrane packet and one having one layer compromised.

FIG. 8 shows examples of the plots obtained by the present integrity test using an eight layered stacked disk arrangement described above with the membranes of the present invention. A challenge solution consisting of 50 micrograms/ml tosyl glutamic acid in 2.5 mMTris buffer at a pH of 8.0. Curve 100 shows the breakthrough curve on an integral membrane. Note the sharp and continuous solute breakthrough occurring at an onset time of approximately 160 seconds. Curve 102 shows an eight-layered device with a defect intentionally induced into the top membrane layer. As seen in 102, premature breakthrough of the tosyl glutamic acid is observed, occurring at a breakthrough time of approximately 120 seconds. This premature breakthrough occurs because the ion-exchange capacity of certain flow paths within the membrane adsorber become exhausted earlier than other flow paths (namely, the flow paths that traverse only 7 membrane layers versus the flow paths that traverse all 8 membrane layers). The remainder of the adsorption bed becomes exhausted at the 160 second time frame. It should be noted that the sensitivity for detecting the presence of small defects can be enhanced by (a) using membranes with more uniform flow properties (membranes with high Pe numbers), which can be obtained, for example, by using membranes with very narrow pore size distributions like the Durapore membrane. This is the preferred method since the membrane essentially determines the maximum sharpness that is affainable for a breakthrough curve study. The methods described below can only minimize the decrease in observable breakthrough curve sharpness that occurs when the membrane adsorber is placed into a device.

(b) Change the solute challenge conditions such that the solute adsorption is further in the non-linear portion of the adsorption isotherm (for an adsorption isotherm that behave Langmuir kinetics) (i.e., increase the solute concentration).

(c) Change the solute and detection system such that lower solute concentrations can be more easily detected.

(d) Design devices that have better flow distribution properties

EXAMPLES

Example 1

Figure 9:
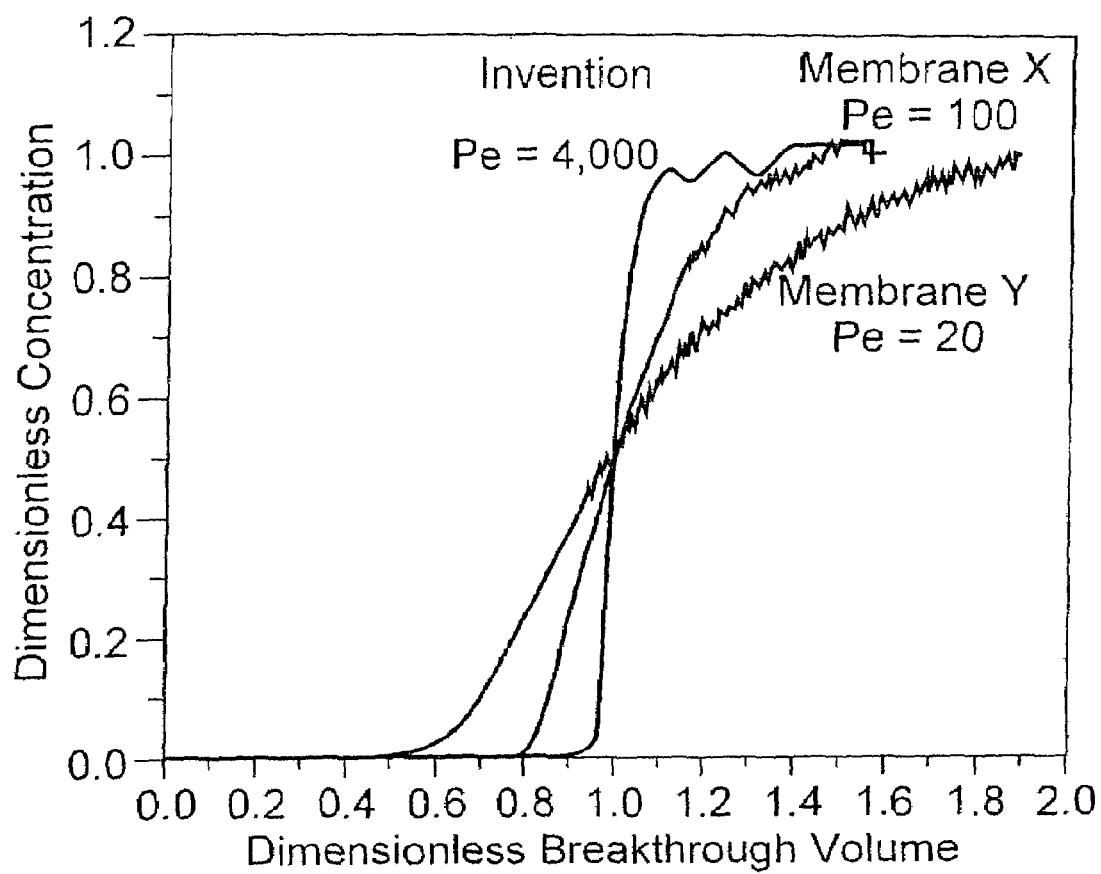
FIG. 9 shows the graph of the Pe data for currently available adsorber membranes.

Tosyl glutamic acid breakthrough curves were measured on three different membrane adsorbers—a 3.5 cm² device made of 8-layers of a positively charged 0.65 µm Durapore membrane (labeled Invention) and two other membrane adsorbers that are commercially available (labeled Membrane X containing 60 layers of membrane and Membrane Y containing 3 layers of membrane). All membrane adsorbers were tested in housings designed to have good flow distribution properties. The devices were first flushed with DI water to completely wet the devices and to eliminate any potential entrapped air that may negatively influence the results. The membrane adsorbers were then flushed with approximately 20 mL of 2.5 mM Tris buffer, pH 8.0. After buffer equilibration, the membrane adsorbers were then challenged with tosyl glutamic acid at a concentration of 50 µg/ml in 2.5 mM Tris, pH 8.0. The resulting breakthrough curves are shown in FIG. 9. As seen in the Figure, the membrane adsorber of the present invention exhibited an extremely sharp breakthrough, with a Pe number of approximately 4000 (as measured by equation (1) above). Membrane X and membrane Y exhibited much more diffuse breakthrough curves, with measured Pe numbers on the order of 100 and 20, respectively. These data indicate that the flow properties inherent with the Durapore membrane are much better than the other tested membrane adsorbers. This has two important implications. First, it is expected that the removal of trace impurities would be more robust with the Durapore membrane adsorber. In fact, virus removal data (presented in Example 2) show that this membrane adsorber is capable of removing over 5 LRV of virus at residence times of less than 1 second. Second, the presence of defects that may negatively influence the retention of trace impurities are much more easy to detect in the Durapore membrane adsorber. Thus, the Durapore membrane adsorber is more amenable to being integrity tested, significantly aiding in virus validation exercises.

Example 2

Figure 10:
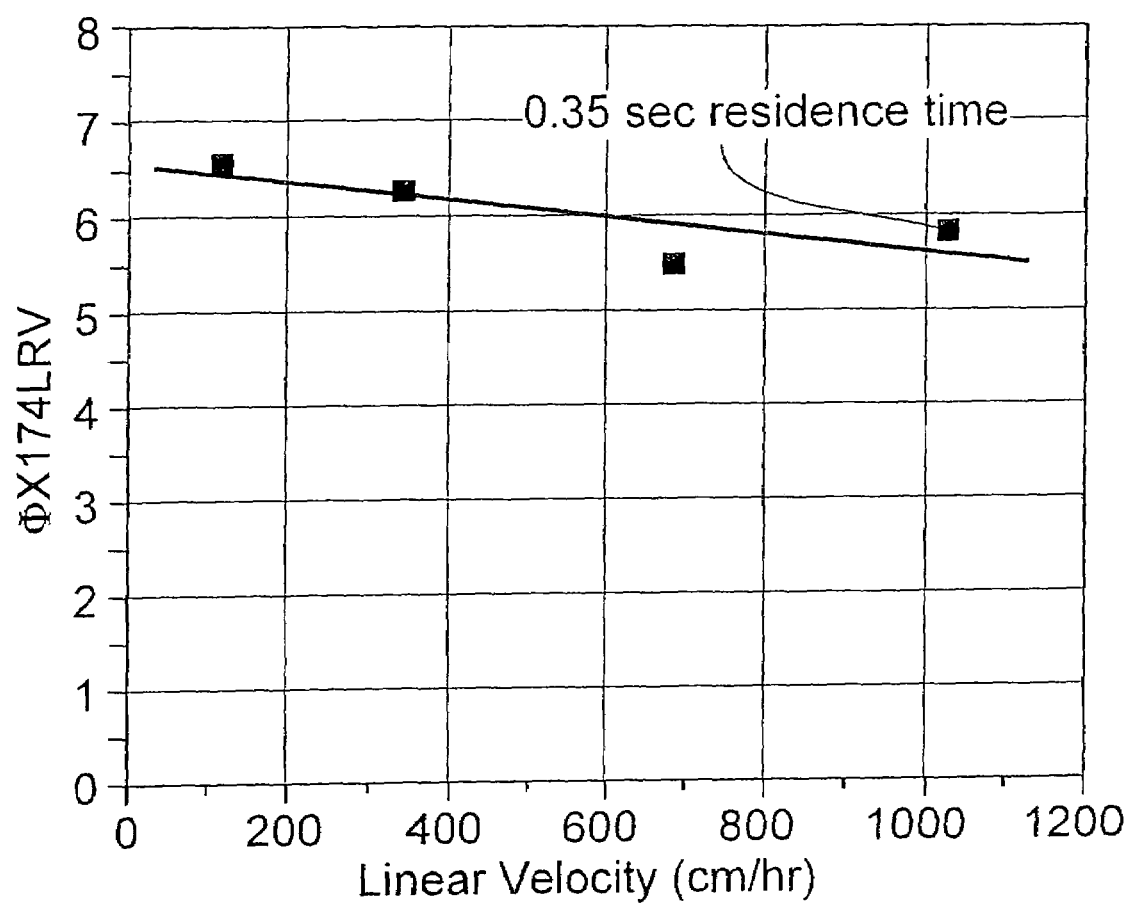
FIG. 10 shows the bacteriophage LRV plotted as a function of challenge linear velocity.

Four different 3.5 cm² membrane adsorbers made of 8-layers of a positively charged 0.65 µm Durapore membrane were challenged with φX-174, a 28 nm diameter bacteriophage. Experimental results (not shown) indicate that this bacteriophage is an excellent marker for understanding the capabilities of membrane adsorbers for removing trace levels of mammalian virus. The devices were first flushed with DI water to completely wet the devices and to eliminate any potential entrapped air that may negatively influence the results. The membrane adsorbers were then flushed with approximately 20 mL of 25 mM Tris buffer, pH 8.0. After buffer equilibration, the membrane adsorbers were then challenged with 300 mL of $1.5 \times 10^7$ pfu/mL φX-174 in 25 mM Tris, pH 8.0. Each of the four devices was challenged at a different flow rate, (either 10, 20, 40, or 60 mL/min). After challenging with the bacteriophage, samples of the feed and effluent pool were assayed for bacteriophage concentration. Finally, bacteriophage LRV values were calculated as $\log_{10}$ (feed concentration/effluent concentration). The bacteriophage LRV is plotted as a function of challenge linear velocity in FIG. 10. As seen in the Figure, virus removal is consistently greater than 5 LRV, a result that is essentially independent of flow rate. It should be noted that at a flow rate of 60 mL/min (linear velocity of approximately 1050 cm/hr), the residence time of the solution within the membrane adsorber is on the order of 0.35 seconds. These data indicate that minimal mass transfer and kinetic limitations exist which may negatively impact virus removal. These data also indicate that the dispersion properties inherent with this particular membrane are extremely good.

Example 3

Tosyl glutamic acid breakthrough curves were measured on five different membrane adsorbers comprised of various numbers of a positively charged 0.65 µm Durapore membrane (1, 3, 5, 7, and 8 layers). The membrane adsorbers were first flushed with DI water to completely wet the devices and to eliminate any potential entrapped air that may negatively influence the results. The membrane adsorbers were then flushed with approximately 20 mL of 2.5 mM Tris buffer, pH 8.0. After buffer equilibration, the membrane adsorbers were then challenged with tosyl glutamic acid at a concentration of 50 µg/ml in 2.5 mM Tris, pH 8.0. The membrane adsorber Pe numbers were calculated based upon 10%, 50%, and 90% breakthrough times (as described previously). The data are tabulated below. As seen in the accompanying table, all of the measured Pe numbers were extremely high, indicating very good flow distribution properties of this membrane adsorber. This is further highlighted in the fact that the Pe number for a 1 layer device was greater than 500. Based on these data, it is expected that this membrane would be an ideal candidate for use as a membrane adsorber for trace impurity removal.

| Number of Membrane Layers | Pe Number |
|---|---|
| 1 | 580 |
| 3 | >10,000 |
| 5 | >10,000 |
| 7 | >10,000 |
| 8 | >10,000 |

Example 4

Figure 11:
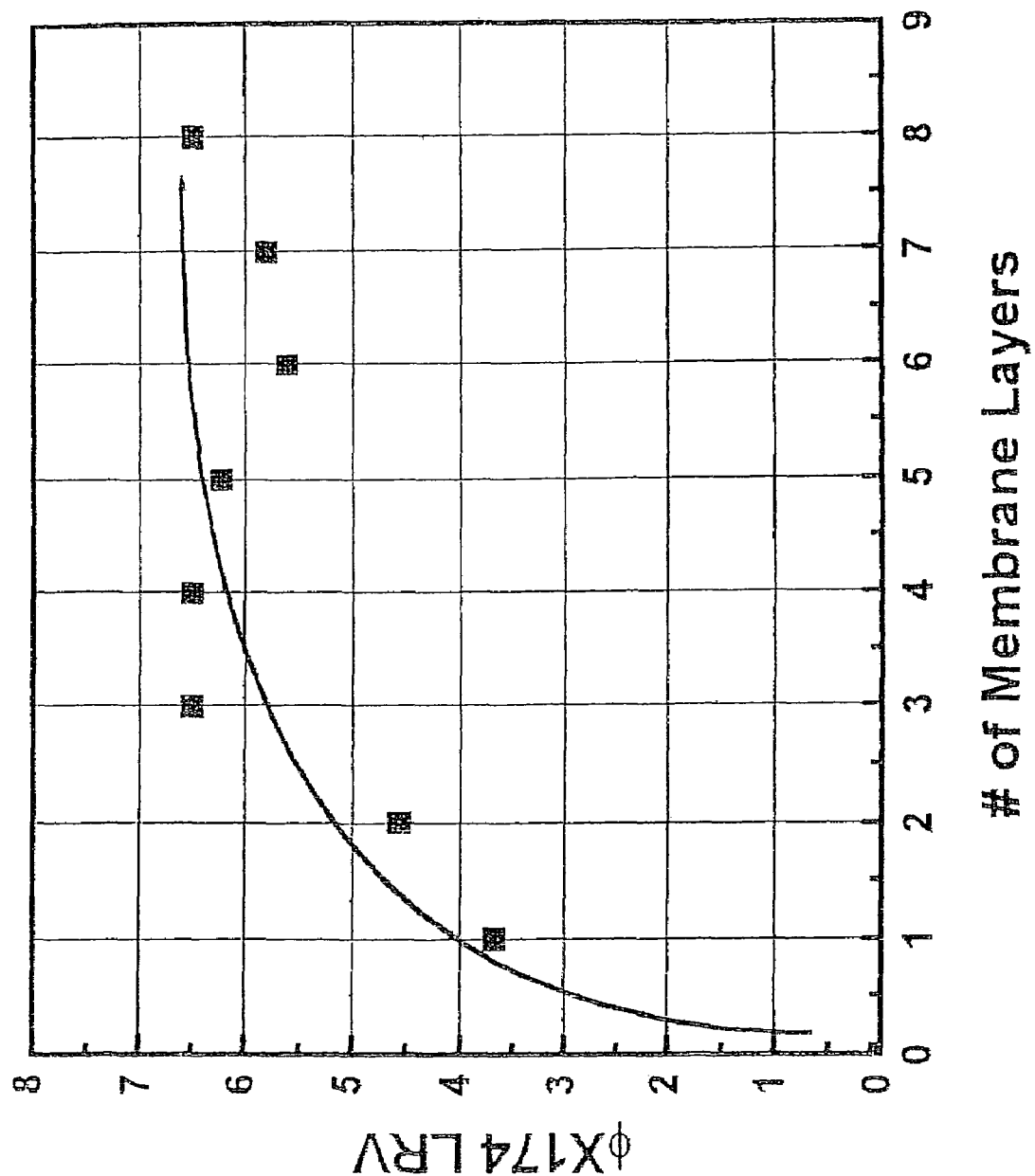
FIG. 11 shows the bacteriophage LRV plotted as a function of number of membrane adsorber layers.

Seven different 3.5 cm² membrane adsorbers made with differing number of membrane layers of a positively charged 0.65 µm Durapore membrane were challenged with φX-174, a 28 nm diameter bacteriophage. The devices were first flushed with DI water to completely wet the devices and to eliminate any potential entrapped air that may negatively influence the results. The membrane adsorbers were then flushed with approximately 20 mL of 25 mM Tris buffer, pH 8.0. After buffer equilibration, the membrane adsorbers were then challenged with 300 mL of 1.5×10⁷ pfu/mL φX-174 in 25 mM Tris, pH 8.0 at a flow rate of 20 mL/min. After challenging with the bacteriophage, samples of the feed and effluent pool were assayed for bacteriophage concentration. Finally, bacteriophage LRV values were calculated as $\log_{10}$ (feed concentration/effluent concentration). The bacteriophage LRV is plotted as a function of number of membrane adsorber layers in FIG. 11. As seen in the Figure, for devices that contain greater than 3 membrane layers, virus removal is consistently greater than 5 LRV, a result which can be attributable to the high membrane Pe number.

What is claimed:

1. A method for determining an effective Peclet number for a membrane adsorber device comprising the steps of: (a) equilibrating the membrane adsorber device with an equilibration buffer at a known pH and conductivity; (b) challenging the membrane with a known concentration of a specific solute in said equilibration buffer; (c) monitoring the breakthrough of the solute downstream of the membrane as a function of a value selected from the group consisting of time, challenge volume and other suitable variable related to total quantity of material challenged to membrane adsorber device; (d) analyzing the solute breakthrough curve to determine pertinent flow characteristics of said membrane adsorber device by calculating the sharpness of the breakthrough curve of said membrane adsorber device; and (e) comparing the results calculated in step (d) to results from known integral devices to determine the effective Peclet number.

2. The method of claim 1 wherein step (c) is performed by a detector.

3. The method of claim 1 wherein step (d) is performed by monitoring the time of solute breakthrough.

4. The method of claim 1 wherein step (d) is performed by monitoring a variable related to the total quantity of material challenged to said membrane adsorber device at a point in time selected from the group consisting of the initial onset of solute breakthrough and a fraction of said solute breakthrough.

5. The method of claim 1 wherein step (d) is performed by monitoring a variable related to the total quantity of material challenged to said membrane adsorber device at a specific fraction of solute breakthrough.

6. The method of claim 5 wherein said fraction is from about 5% to about 50%.

7. The method of claim 5 wherein said fraction is from about 5% to about 20%.

8. The method of claim 5 wherein said fraction is from about 5% to about 10%.

9. The method of claim 1 wherein step (d) is performed by calculating a breakthrough curve sharpness and an initial onset of solute breakthrough.

10. A method for calculating an effective Peclet number for a membrane adsorber device comprising the steps of: (a) equilibrating the membrane adsorber device with an equilibration buffer at a known pH and conductivity; (b) challenging the membrane with a known concentration of a specific solute in said equilibration buffer; (c) monitoring the breakthrough of the solute downstream of the membrane as a function of a value selected from the group consisting of time, challenge volume and other suitable variable related to total quantity of material challenged to membrane adsorber device; (d) fitting the equation:

$$C_A/C_0 = \tfrac{1}{2} * \{1 + erf[[(Pe)^{1/2}*(V-V_{bar})]/[2*[V*V_{bar}]^{1/2}]]\}$$

where $C_A$ is the effluent solute concentration $C_0$ is the inlet solute concentration $V$ is the challenge volume $V_{bar}$ is the challenge volume at 50% breakthrough ($C_A/C_0=0.5$)

Pe is the effective Peclet number to said experimentally determined breakthrough curve to determine the effective Peclet number.

11. The method of claim 10 wherein step (d) is performed using a least-squares fit.

12. The method of claim 10 wherein step (d) is performed using a multipoint method.

13. The method of claim 12 further comprising the steps of: (e) using said equation to develop a generic plot of Pe versus $(V_{90}-V_{10})/V_{50}$; (f) determine $V_{10}$, $V_{50}$ and $V_{90}$ from said experimentally determined breakthrough curve, and (g) finding Pe from said generic plot using said experimentally determined values of $V_{10}$, $V_{50}$ and $V_{90}$ wherein $V_{10}$, $V_{50}$, and $V_{90}$ are the breakthrough volumes corresponding to 10, 50, and 90% solute breakthrough, respectively.

* * * * *